(12) United States Patent
Cannata et al.

(10) Patent No.: US 7,449,583 B2
(45) Date of Patent: Nov. 11, 2008

(54) PROCESS FOR THE PREPARATION OF 4-(8-CHLORO-5 6-DIHYDRO-11H-BENZO-(5 6)-CYCLOHEPTA-(1 2B)-PYRIDIN-11-YLIDENE-1-PIPERIDINIECARBOXYLIC ACID ETHYL ESTER (LORATADINE)

(75) Inventors: Vincenzo Cannata, Sasso Marconi (IT); Livius Cotarca, Cervignano Del Friuli (IT); Ivan Michieletto, Treviso (IT); Stefano Poli, Veggiano (IT)

(73) Assignee: ZaCh System S.p.A., Bresso (IT)

( * ) Notice: Subject to any disclaimer, the term of this patent is extended or adjusted under 35 U.S.C. 154(b) by 549 days.

(21) Appl. No.: 10/493,314

(22) PCT Filed: Oct. 29, 2002

(86) PCT No.: PCT/EP02/12056

§ 371 (c)(1), (2), (4) Date: Mar. 23, 2005

(87) PCT Pub. No.: WO03/040140

PCT Pub. Date: May 15, 2003

(65) Prior Publication Data

US 2005/0171352 A1    Aug. 4, 2005

(30) Foreign Application Priority Data

Nov. 5, 2001   (IT) .......................... MI2001A2308

(51) Int. Cl.
*C07D 413/04* (2006.01)
(52) U.S. Cl. .................................. 546/271.4; 546/193

(58) Field of Classification Search ................. 546/193, 546/271.4
See application file for complete search history.

(56) References Cited

U.S. PATENT DOCUMENTS

| 4,731,447 A | 3/1988 | Schumacher et al. ......... 546/93 |
| 5,750,470 A * | 5/1998 | Morimoto et al. ........... 504/253 |

FOREIGN PATENT DOCUMENTS

| WO | 0005215 | 2/2000 |
| WO | 0037457 | 6/2000 |

OTHER PUBLICATIONS

Brunner et al. "Asymmetric catalysis . . ." CA 107:39301 (1987).*
Davenport et al. "Arene ruthenium complexes . . ." CA 134:237623 (2000).*
Constant et al. "Trisphat-N . . ." CA 146:533343 (2007).*

* cited by examiner

*Primary Examiner*—Celia Chang
(74) *Attorney, Agent, or Firm*—Oblon, Spivak, McClelland, Maier & Neustadt, P.C.

(57) ABSTRACT

A process and new oxazolinic intermediates for the preparation of 4-(8-chloro-5,6-dihydro-11H-benzo-[5,6]-cyclohepta-[1,2-b]-pyridin-11-ylidene)-1-piperidinecarboxylic acid ethyl ester (loratadine) is described. The process starts from 2-(4,4-dimethyl-4,5-dihydrooxazol-2-yl)-3-methyl-pyridine, a new intermediate to obtain loratadine. 2-(4,4-dimethyl-4, 5-dihydrooxazol-2-yl)-3-methyl-pyridine is condensed with 3-chloro-benzyl-chloride and the resultant product is treated with Grignard reagent of 4-chloro-N-methyl-piperidine. [3-(2-(3-chloro-phenyl)-ethyl]-pyridin-2-yl]-1-(methyl-piperidin-4-yl)-methanone is obtained for subsequent hydrolysis. Starting from this last compound it is possible to obtain loratadine with known methods.

3 Claims, No Drawings

PROCESS FOR THE PREPARATION OF 4-(8-CHLORO-5 6-DIHYDRO-11H-BENZO-(5 6)-CYCLOHEPTA-(1 2B)-PYRIDIN-11-YLIDENE-1-PIPERIDINIECARBOXYLIC ACID ETHYL ESTER (LORATADINE)

CROSS REFERENCE TO RELATED APPLICATION

This application is a 371 of PCT/EP/02/012056, filed Oct. 29, 2002 and claims priority to Italian Patent Application No. MI2001A002308, filed Nov. 5, 2001.

The present invention relates to a process for preparing loratadine, a medicinal product with antihistamine activity. Loratadine is ethyl 4-(8-chloro-5,6-dihydro-11H-benzo[5,6]cyclohepta[1,2-b]pyridin-11-ylidene)-1-piperidinecarboxylate (*The Merck Index, 12th ed.,* 5608, p. 953). More specifically, the invention relates to a process for synthesizing loratadine from a novel intermediate, 2-(4,4-dimethyl4,5-dihydrooxazol-2-yl)-3-methylpyridine.

Loratadine was described for the first time in Schering patent U.S. Pat. No. 4,282,233. In the said patent, the synthesis of loratadine is described starting with 8-chloro-11-(1-methylpiperid-4-ylidene)-6,11-dihydro-5H-benzo[5,6]cyclohepta[1,2-b]pyridine a), which reacts with ethyl chloroformate in benzene. Scheme 1 illustrates the reaction.

Scheme 1

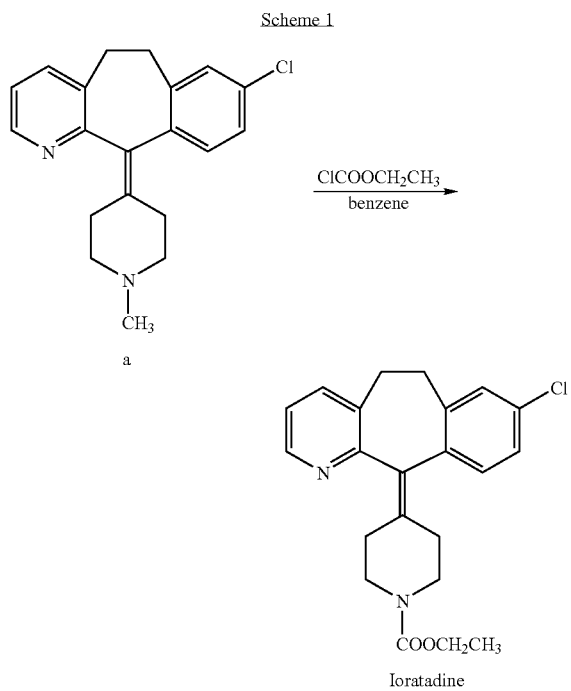

From examination of the patent literature pertaining to the synthesis of loratadine, it is found that there are two main intermediates via which compound a) is obtained. The first is [3-[2-(3-chlorophenyl)ethyl]-pyridin-2-yl]-(1-methyl4-piperidyl)methanone of formula b), and the second is 8-chloro-5,6-dihydrobenzo[5,6]cyclohepta[1,2-b]-pyridin-11-one of formula c).

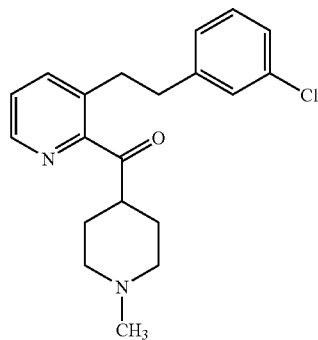

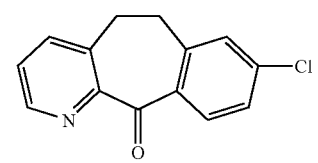

Schering patent U.S. Pat. No. 4,731,447 describes the synthesis of compound a) from compound b), the latter compound being obtained from 3-methyl-2-cyanopyridine in four steps. Compound b) gives compound a) by cyclization with a superacid having a Hammett acidity constant lower than −12. U.S. Pat. No. 4,731,447 in turn describes the synthesis of compound c) from 3-[2-(3-chlorophenyl)ethyl]-2-pyridinecar-boxamide, in a single step, by treatment with a superacid, or in three steps without the use of a superacid.

However, given their chemical corrosiveness, superacids are problematic to use industrially. The synthesis of a) from compound c) is described in Schering U.S. Pat. No. 4,659,716. a) is obtained by reacting compound c) with the Grignard reagent of 4-chloro-N-methylpiperdine, to give 8-chloro-11-(1-methyl-piperidin4-yl)-6,11-dihydro-5H-benzo-[5,6]cyclohepta[1,2-b]pyridin-11-ol, which, by subsequent dehydration, gives a). Another process that involves starting with compound c) and obtaining loratadine without proceeding via compound a) is described in Schering patent application WO 00/37457. In this case, the synthesis proceeds via a Wittig reaction between compound c) and a phosphorus ylide; the reaction generates an unstable "β-hydroxyphosphonate" intermediate. On account of its instability, the intermediate "β-hydroxyphosphonate" needs to be stabilized by adding a protonating agent (water or acetic acid) and only thereafter, by thermal decomposition it can give loratadine. However, as described in WO 00/37457, the said product is not in pure form, but needs to be purified several times by distillation and finally recrystallized to remove the impurities of solvent, of compound c) and of phosphorus-containing compounds. Thus, in addition to being laborious, this process also involves losses of product.

The syntheses described hitherto therefore involve various drawbacks including a large number of steps, the use of reagents that are difficult to handle at the industrial level, the formation of unwanted side-reaction products and therefore reactions to purify the product or the intermediate, which reduce the yields.

Surprisingly, a process that represents one of the aspects of the present invention has now been found, this process making it possible to synthesize loratadine from 2-(4,4-dimethyl-4,5-dihydrooxazol-2-yl)-3-methylpyridine of formula I.

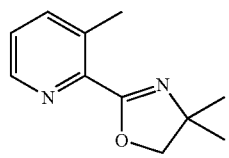

Compound I reacts with 3-chlorobenzyl chloride in the presence of a strong base to give the compound of formula II.

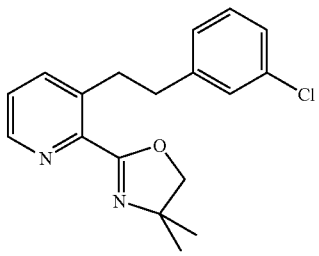

Compound II, reacting in the presence of the Grignard reagent of 4-chloro-N-methylpiperidine in an inert solvent, gives compound III accompanied by small amounts of compound VI.

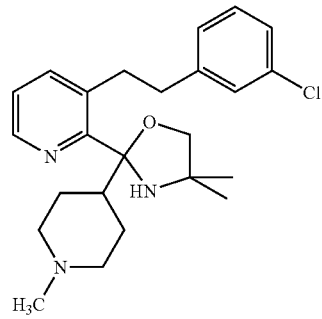

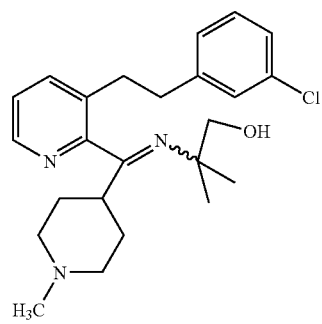

Compound III, along with compound VI which may be present, is then converted under hydrolytic conditions into the intermediate b) and finally from the said intermediate into loratadine by known methods.

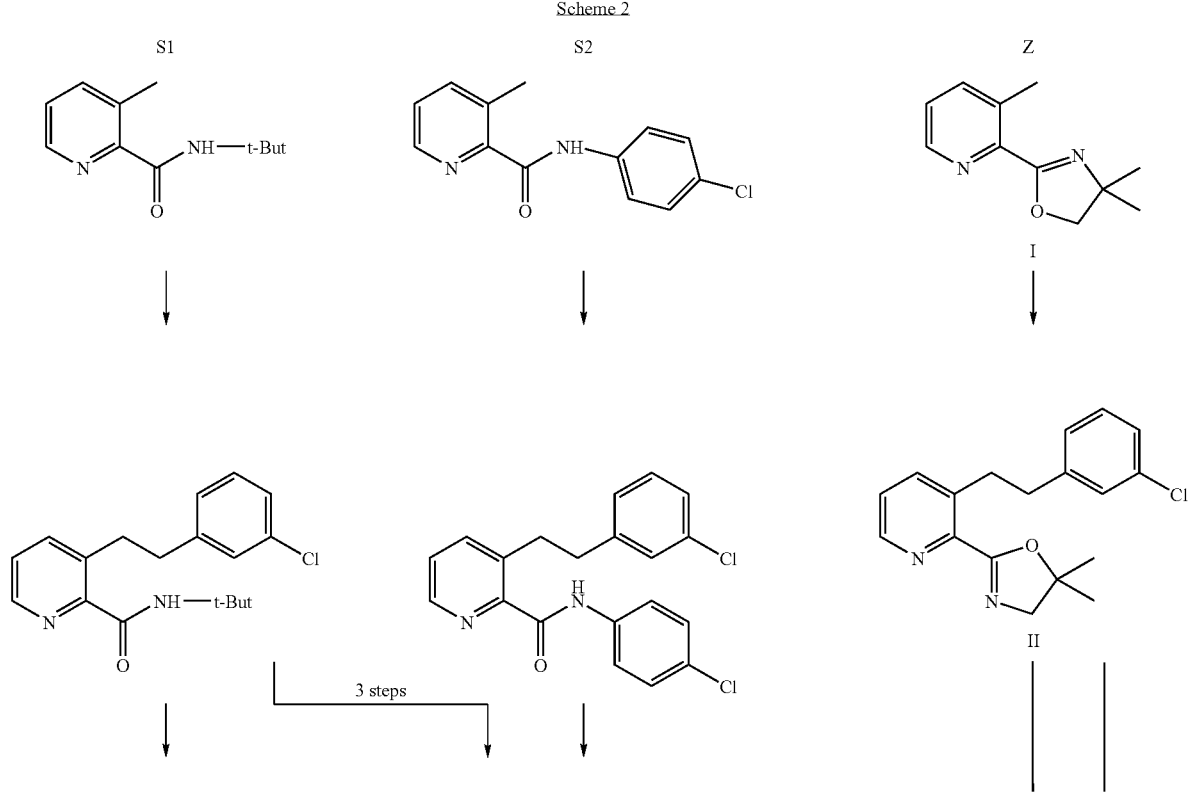

-continued

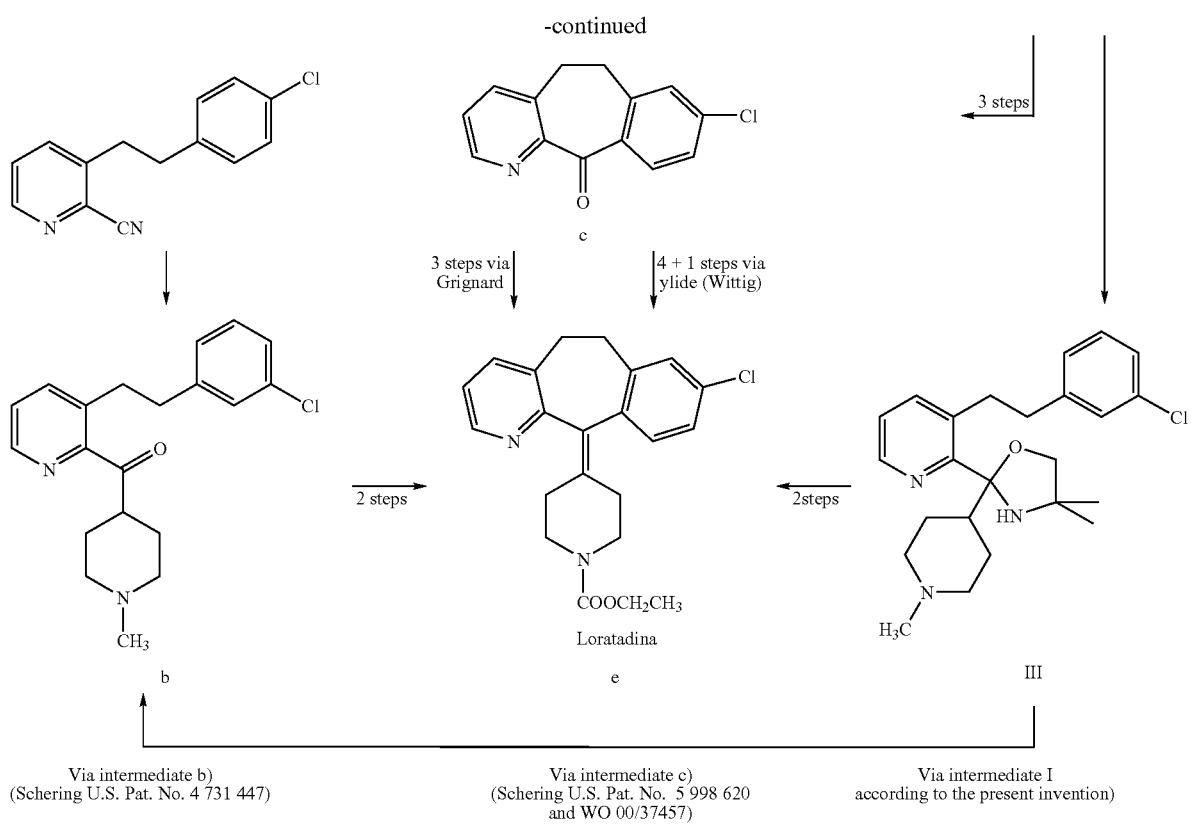

| Via intermediate b) | Via intermediate c) | Via intermediate I |
| (Schering U.S. Pat. No. 4 731 447) | (Schering U.S. Pat. No. 5 998 620 and WO 00/37457) | according to the present invention) |

Scheme 2 compares the process that is the object of the present invention with the processes described by Schering, indicated by the abbreviations Z, S1 and S2, respectively.

A second aspect of the present invention is represented by the novel compounds of formulae I, II and III and their use for the preparation of loratadine.

A third aspect is represented by a process for obtaining the intermediate b) from compound I, which, by treatment with lithium diisopropylamide (LDA) at 0° C. and then with 3-chlorobenzyl chloride, gives compound II. Subsequent treatment of compound II with the Grignard reagent of 4-chloro-N-methylpiperidine produces compound III, which, on hydrolysis, gives the intermediate b).

A fourth aspect of the invention is represented by an alternative method, relative to processes S1 and S2 of scheme 2, for obtaining the intermediate c) from compound II, which is hydrolysed to give 3-[2-(3-chlorophenyl)ethyl]-pyridine-2-carboxylic acid of formula IV.

IV

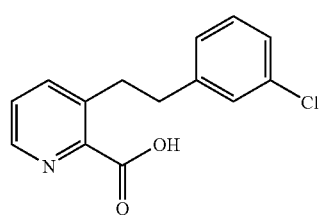

The acid function of compound IV is converted into the corresponding acid chloride and then coupled via a Friedel-Crafts reaction to give the intermediate c).

A fifth aspect of the present invention is a process for synthesizing loratadine by preparation of compound II to give c) according to the process described above, followed by conversion of c) into loratadine according to known techniques.

A preferred embodiment of the invention consists in using 2-(4,4-dimethyl4, 5-dihydrooxazol-2-yl)-3-methylpyridine of formula I as starting compound.

Obviously, the use of oxazoline analogues such as the 4-methyl-, 4,4-diethyl- or 4-ethyloxazoline, bearing the same substituent in position 2, fall within the spirit of the present invention. The choice of the 4,4-dimethyloxazoline (compound I) is based solely on criteria of process economics.

The route that has been found to be the most advantageous for obtaining compound I is that described in the article by Fryzuk M. D., Jafarpour L. and Rettig S. J., *Tetrahedron: Asymmetry*, 1998, 9, 3191. The experimental conditions for obtaining 2-(4,4-dimethyl-4,5-dihydrooxazol-2-yl)-3-methylpyridine were drawn from this article. The latter compound is obtained by reaction between 2-cyano-3-methylpyridine and 1,1-dimethylaminoethanol, using anhydrous $ZnCl_2$ as catalyst at 140° C. for 15 hours, in the absence of solvent.

Compound I thus obtained was reacted with 3-chlorobenzyl chloride or an analogue thereof (see scheme 3) in the presence of a strong base, preferably lithium diisopropylamide (LDA). The reaction was performed in an inert solvent (THF, toluene, diethyl ether or hexane); tetrahydrofuran (THF) and a temperature range of between −15° C. and 25° C. and preferably between −5° C. and +5° C. are particularly preferred, giving 3-[2-(3-chlorophenyl)ethyl]-2-(4,4-dimethyl-4,5-dihydrooxazol-2-yl)pyridine of formula II.

Scheme 3

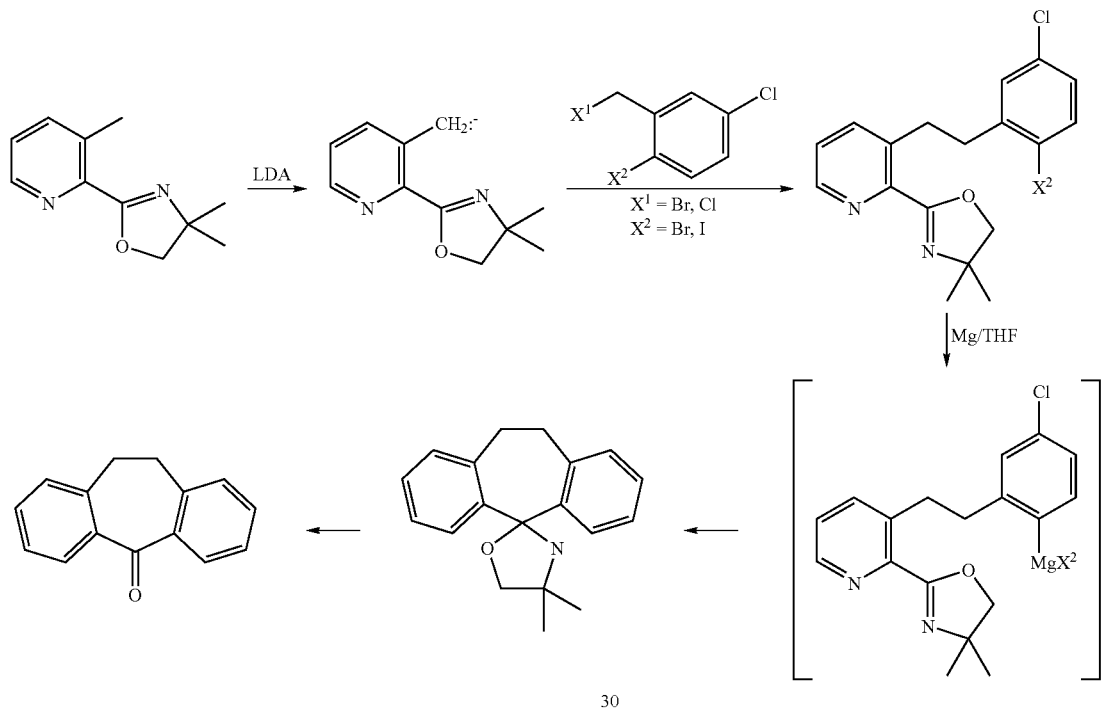

By reacting compound II with the Grignard reagent of 4-chloro-N-methylpiperidine, prepared according to standard techniques, in THF and at a temperature of between −40° C. and 0° C. and preferably between −20° C. and −10° C., [3-[2-(3-chlorophenyl)ethyl]-2-[4,4-dimethyl-2-(1-methyl-piperidin4-yl)-oxazolidin-2-yl]-pyridi-ne of formula III is obtained.

Addition of the Grignard reagent to compound II takes place selectively and therefore, as is seen in scheme 2, an additional step is avoided, which is, however, necessary by the Schering process S1.

Finally, compound III may be converted into b) by hydrolysis, and loratadine is obtained from this product according to known techniques.

The following experimental examples are now given for the purposes of illustrating the invention more clearly, without, however, limiting it.

EXAMPLE 1

Synthesis of 2-(4,4dimethyl4,5-dihydrooxazol-2-yl)-3-methylpyridine

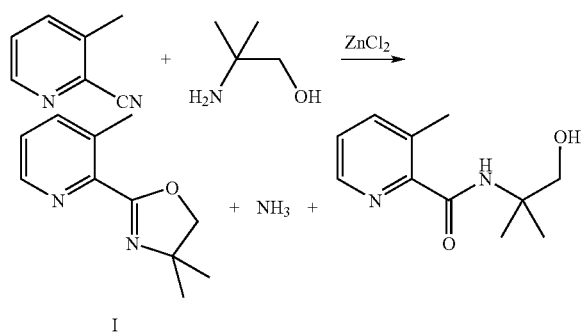

100 g (0.847 mol) of 3-methyl-2-cyanopyridine, 151.08 g (1.695 mol) of 2-methyl-2-aminopropanol and 5.77 g of anhydrous $ZnCl_2$ (0.042 mol) are placed in a 300 ml jacketed reactor, the temperature is raised to 140° C. (at about 60° C. a solution is obtained) and is maintained at 140° C. for 15-18 hours. During the reaction, ammonia vapours are evolved, and are collected in a trap of dilute hydrochloric acid. The end of the reaction is monitored by TLC. At the end of the reaction the mixture is cooled to 60° C. and, at this point, it is filtered through a Gooch crucible to give about 190.06 g of white salts. Cooling is then continued to room temperature. 250 g of toluene and 99 g of saturated NaCl solution are added. The aqueous phase is re-extracted with toluene and the organic phases are combined and then washed again, thus removing the unreacted dimethylaminoethanol. The toluene solution is evaporated to give 166.5 g of a pale red oil with an HPLC titre of compound I of 95.3%, the remainder consisting of the compound of formula V.

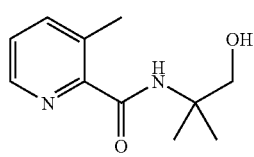

Compound V may in turn be converted into the oxazoline by treatment with mesyl chloride and triethylamine in $CH_2Cl_2$ at −5° C.

Compound I may also be distilled at 105-112° C. and at 1.5 mmHg to give an oxazoline titre >97%. Yield 98.5%

Compound I: $^1$H-NMR (200 MHz, $CDCl_3$) δ (ppm): 8.52 (dd, J=4.3 and 1.8 Hz, 1 H); 7.57 (dd, J=7.9 and 1.8 Hz, 1 H); 7.25 (dd, J=7.9 and 4.3 Hz, 1H); 4.14 (s, 2 H); 2.59 (s, 3 H); 1.42 (s, 6 H).

EXAMPLE 2

Synthesis of 3-[2-(3-chlorophenyl)ethyl]-2-(4,4-dimethyl-4,5-dihydrooxazol-2-yl)-pyridine

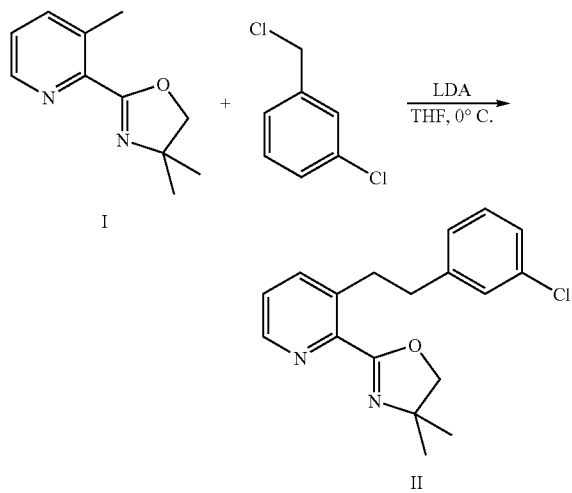

521.7 ml of anhydrous THF and 521.7 ml of 2M LDA solution (1.04 mol) are placed in a 3-litre jacketed reactor equipped with a mechanical stirrer and thermometer, and maintained under a nitrogen atmosphere, the internal temperature is brought to −5° C. and a solution consisting of 158.8 g of oxazoline (0.835 mol) and 834.7 ml of anhydrous THF is then added slowly, keeping the temperature at about 0° C. After adding a few drops of solution, a strong blue-violet colour is obtained. The total addition time is about one hour. 154.6 g (0.96 mol) of 3chlorobenzyl chloride are then added over about 1.5 hours, while still maintaining the temperature at 0° C. At the end of the reaction, 521.7 g of water are added while bringing the temperature to 20-25° C. The two phases are then separated and the organic phase is evaporated to give an oil. The crude product thus obtained is taken up in toluene and filtered through Tonsil. The filtrate is concentrated to give 268.1 g of an oil with an HPLC titre of 79%. 91.8% conversion, yield=80.2%

$^1$H-NMR (200 MHz, CDCl$_3$) δ (ppm): 8.58 (dd, 1 H); 7.31-7.10 (m, 5 H); 4.17 (s, 2 H); 3.37-3.28 (m, 2 H); 2.95-2.86 (m, 2 H); 1.47 (s, 6 H)

$^{13}$C-NMR (50 MHz, CDCl$_3$) δ (ppm): 160.78 (s); 147.75 (d); 146.07 (s); 144.10 (s); 139.22 (d); 138.52 (s); 134.44 (s); 129.98 (d); 129.11 (d); 127.07 (d); 126.61 (d); 125.22 (d); 79.02 (t); 69.07 (s); 37.37 (t); 35.84 (t); 28.98 (q, two coincident methyls).

EXAMPLE 3

Synthesis of [3-[2-(3-chlorophenyl)ethyl]-2-[4,4-dimethyl-2-(1-methyl-piperidin-4yl -oxazolidin-2-yl] pyridine

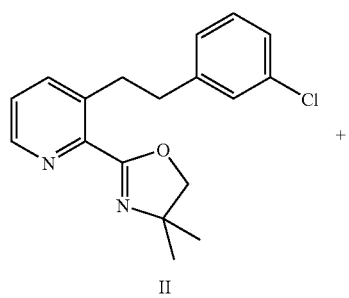

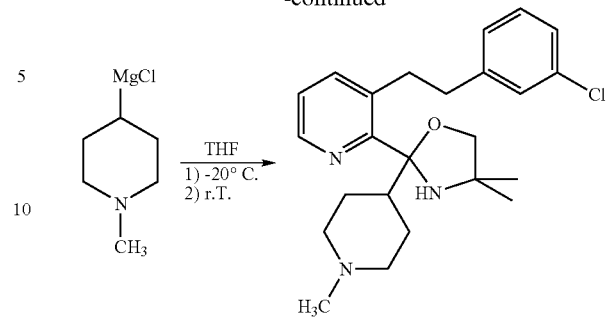

Preparation of the Grignard Reagent 10 g of magnesium filings (0.41 mol) and 163 g of anhydrous THF are placed in a 400 ml reactor equipped with a mechanical stirrer, a bubble condenser, a thermometer and a 100 ml dropping funnel, under a nitrogen atmosphere. The system is brought to 60° C. and about 1 ml of Vitride® (70% w/w solution of sodium dihydrobis(2-methoxyethoxy)aluminate in toluene) and about 5% of the solution of 4-chloro-N-methylpiperidine (57.7 g, 0.41 mol) in 163 g of anhydrous THF are added. After a few minutes, a gentle exothermicity is noted. The remainder of the solution is then added slowly. Once the addition is complete, the reaction mixture is maintained at 60° C. overnight. The Grignard suspension, which is easily stirrable, is used without further modification in the subsequent coupling stage.

Coupling 116 g of crude 3-[2-(3-chlorophenyl)ethyl]-2-(4,4dimethyl-4,5-dihydrooxazol-2-yl)pyridine (0.32 mol) and 368.6 g of anhydrous THF are placed in a 1-litre reactor equipped with a mechanical stirrer, a thermometer and a 500 ml dropping funnel, under a nitrogen atmosphere. The solution is cooled to −20° C. Addition of the Grignard reagent prepared in the preceding stage is then started, while keeping the temperature at about −20° C. Next the cooling is stopped and the system is allowed to return to room temperature. The reaction progress is followed by HPLC. After leaving overnight at room temperature, the HPLC monitoring shows about 2.9% (by area) of unreacted 3-[2-(3-chlorophenyl)ethyl]-2-(4,4-dimethyl-4,5-dihydrooxazol-2-yl)pyridine. The mixture is diluted with toluene (200 ml) and 270 g of acetic acid (aqueous 10% w/w solution) are added slowly. The resulting mixture is stirred for about 30 minutes and then left to stand for a further 30 minutes. The phases are separated. The organic phase gives 146 g of a crude product, in the form of a dark oil, consisting of a mixture of compound III and a small amount of compound VI. The mixture of the two products is used in the subsequent reaction without further purification.

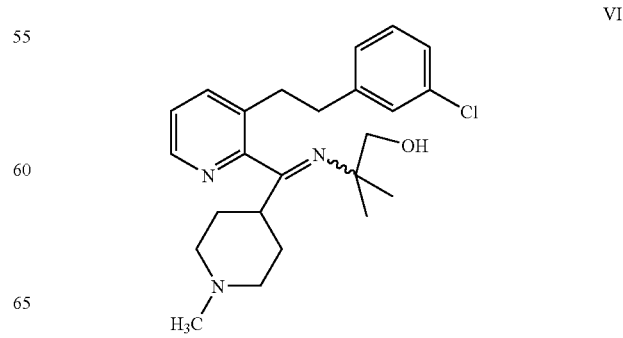

EXAMPLE 4

Synthesis of [3-[2-(3-chlorophenyl)ethyl]-2-pyridyl](1-methyl-4-piperidyl)methanone

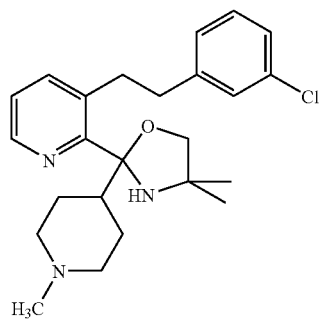

III

+

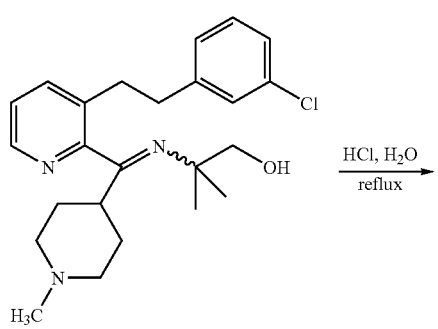

→ (HCl, H₂O, reflux)

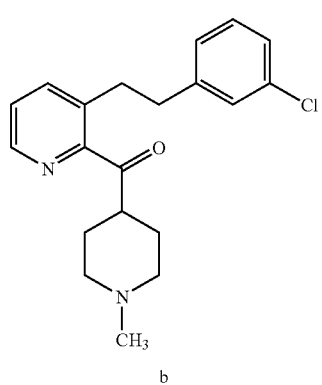

b 24.1 g of crude product obtained from the reaction of Example 3, 51.4 g of H₂O and 10.2 g of HCl (31% w/w) are placed in a 250 ml round-bottomed flask equipped with a magnetic stirrer and a bubble condenser. The solution thus obtained is brought to reflux. After refluxing for 14 hours, the TLC and ¹H-NMR controls indicate the disappearance of the substrate. The mixture is cooled to room temperature, diluted with dichloromethane (CH₂Cl₂) (50 ml) and sodium hydroxide (NaOH) (30% w/w) is added up to pH=8.5-9. The organic phase is dried over sodium sulphate (Na₂SO₄) and the solvent is evaporated off under vacuum. The crude product, in the form of a dark oil, is analysed by HPLC (area about 58%). The ketone may be crystallized from H₂O in the form of the hydrochloride.

EXAMPLE 5

Synthesis of 3-[2-(3-chlorophenyl)ethyl]-pyridine-2-carboxylic acid

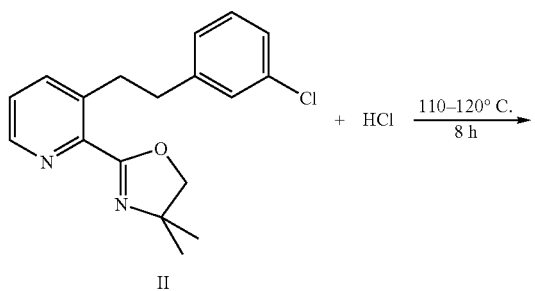

II

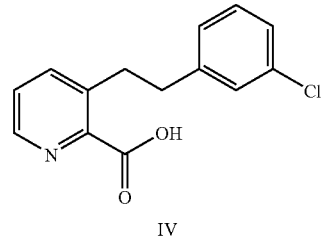

IV 268.1 g (0.67 mol) of compound II and 645.6 g of H₂O are placed in a 2-litre reactor equipped with a mechanical stirrer, at room temperature. 787.3 g of 31% HCl are added to this dispersion. The resulting mixture is then brought to reflux and left for at least 8 hours. The reaction is monitored by TLC. At the end of the reaction, the mixture is cooled to 60° C., 1340.6 g of toluene are added, the mixture is brought to about pH 5 with 30% NaOH, and the phases are separated. The aqueous phase is re-extracted with toluene, the two organic phases are combined and the toluene is evaporated off to give 219 g of a dark oil with a titre of 80%. A solid white product may be obtained from this oil by crystallization from toluene at 0° C.

EXAMPLE 6

Synthesis of 8-chloro-5,6-dihydrobenzo[5,6]cylcohepta[1,2-b]pyrid-11-one

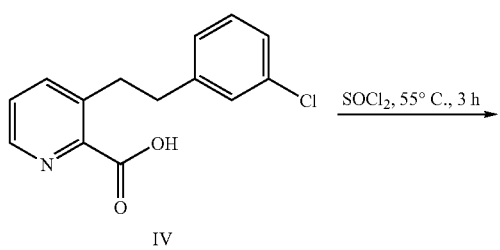

IV

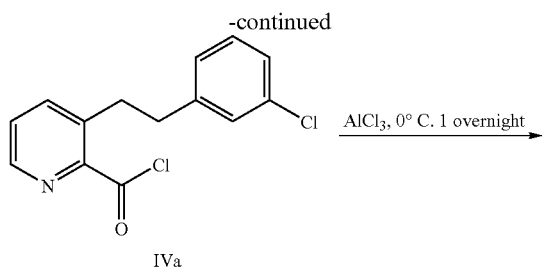

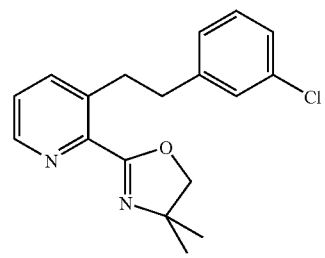

b) reacting compound II with the Grignard reagent of 4-chloro-N-methylpiperidine, in an inert solvent, to give [3-[2-(3-chlorophenyl)ethyl]-2-[4,4-dimethyl-2-(1-methyl-piperidin-4-yl)-oxazolidine-2-yl]pyridine of formula III, and

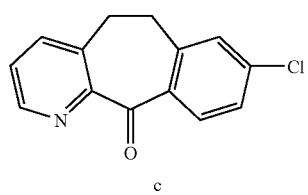

IVa

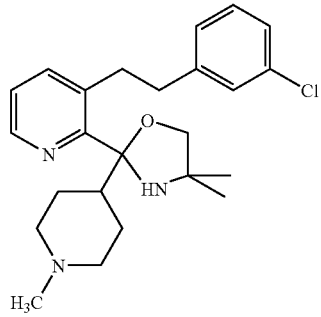

III

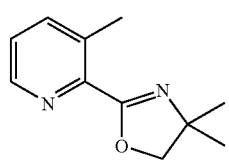

c 5 g of compound IV with a titre of 70% are placed in a 250 ml reactor, 70 g of SOCl₂ are added dropwise at room temperature and the mixture is brought to 55-60° C. and left to react for three hours. The disappearance of the acid is monitored by TLC and the excess SOCl₂ is then distilled off to give 6 g of a dark residue. This residue is dissolved in about 10 ml of dichloroethane, the reaction mixture is cooled to 0° C. and 5.3 g of AlCl₃ are then added portionwise. The resulting mixture is then left overnight at between −5° C. and 0° C. At the end of the reaction, the mixture is acidified with 1N HCl, while keeping the temperature between 10-15° C., the phases are separated, a second acidic extraction is carried out with 50 ml of water and the aqueous phases are combined and basified with NaOH to pH 12, and then re-extracted with toluene. After evaporating off the solvent, a solid is obtained, which, when crystallized from diisopropyl ether, gives 2 g of a pale yellow solid with an NMR titre>99%, 62% yield.

c) hydrolyzing compound III to give the intermediate of formula b)

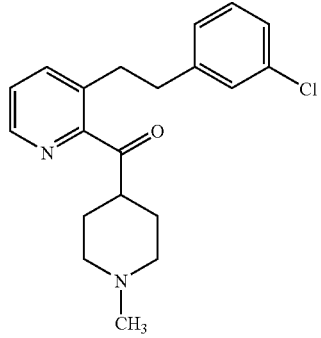

b

The invention claimed is:

1. Process for synthesizing loratadine, which consists in
   a) reacting 2-(4,4-dimethyl-4,5-dihydrooxazol-2-yl)-3-methylpyridine of formula I

I with 3-chlorobenzyl chloride, in the presence of a strong base, to give 3-[2-(3-chlorophenyl) ethyl]-2-(4,4-dimethyl-4,5-dihydrooxazol-2-yl)pyridine of formula II which is converted by known methods into loratadine.

2. Process according to claim 1, in which the strong base is lithium diisopropylamide.

3. Process according to claim 1, in which the inert solvent is tetrahydrofuran.

\* \* \* \* \*